(12) United States Patent  
Mobley (10) Patent No.: US 11,191,861 B2  
(45) Date of Patent: Dec. 7, 2021

(54) TEAR-AWAY PACKAGE FOR FRAGRANCE IMPREGNATED WAFER

(71) Applicant: David D. Mobley, Colleyville, TX (US)

(72) Inventor: David D. Mobley, Colleyville, TX (US)

( * ) Notice: Subject to any disclaimer, the term of this patent is extended or adjusted under 35 U.S.C. 154(b) by 258 days.

(21) Appl. No.: 16/502,930

(22) Filed: Jul. 3, 2019

(65) Prior Publication Data

US 2021/0000997 A1     Jan. 7, 2021

(51) Int. Cl.
| | |
|---|---|
| *A61L 9/12* | (2006.01) |
| *B65D 75/58* | (2006.01) |
| *B65D 75/26* | (2006.01) |
| *B65D 27/34* | (2006.01) |
| *A61L 9/04* | (2006.01) |

(52) U.S. Cl.
CPC ............. *A61L 9/12* (2013.01); *A61L 9/042* (2013.01); *B65D 27/34* (2013.01); *B65D 75/26* (2013.01); *B65D 75/5805* (2013.01); *B65D 75/5816* (2013.01); *B65D 2221/00* (2013.01)

(58) Field of Classification Search
CPC ....... A61L 9/12; A61L 2209/13; B65D 27/34; B65D 75/26; B65D 75/5805; B65D 75/5816; B65D 2221/00; B65D 27/32; B65D 27/36; B65D 75/5811; B65D 75/5827; A01M 1/2055
USPC ................................ 239/34, 53–56; 383/200
See application file for complete search history.

(56) References Cited

U.S. PATENT DOCUMENTS

| | | | |
|---|---|---|---|
| 2,120,204 A | | 6/1938 | Langhorst |
| 2,615,754 A | | 10/1952 | Lindenberg |
| 2,757,957 A | * | 8/1956 | Samann ............. A01M 1/2055 239/53 |
| 3,065,915 A | * | 11/1962 | Samann ................. A61L 9/12 239/35 |
| 3,575,345 A | * | 4/1971 | Buck, Jr. ............... E03D 9/04 239/34 |
| 4,145,001 A | | 3/1979 | Weyenberg et al. |
| 4,283,011 A | | 8/1981 | Spector |
| 4,802,626 A | | 2/1989 | Forbes et al. |
| 4,889,755 A | | 12/1989 | Charbonneau |
| 5,372,303 A | | 12/1994 | Paul |
| 5,395,047 A | | 3/1995 | Pendergrass, Jr. |
| 5,503,332 A | | 4/1996 | Glenn |
| 5,529,243 A | * | 6/1996 | Hoyt ..................... A61L 9/12 239/56 |
| 5,611,486 A | | 3/1997 | Paul |
| 5,782,409 A | * | 7/1998 | Paul ..................... A61L 9/12 239/56 |
| 5,845,847 A | | 12/1998 | Martin et al. |
| 6,012,643 A | | 1/2000 | Barlow et al. |
| 6,280,085 B1 | | 8/2001 | Beer |
| RE39,905 E | | 11/2007 | Mobley |
| 7,926,735 B1 | * | 4/2011 | Mobley ................. A61L 9/04 239/53 |
| 8,251,217 B2 | * | 8/2012 | Hemmerlin ........ B65D 75/5805 206/532 |

(Continued)

*Primary Examiner* — Cody J Lieuwen (74) *Attorney, Agent, or Firm* — Dan Brown Law Office; Daniel R. Brown (57) ABSTRACT

A fragrance compound impregnated porous carrier enclosed within an envelope where a tear initiating feature of the envelope is aligned with a trimmed portion of the porous carrier, to thereby prevent a tear in the envelope from inducing a tear in the porous carrier.

9 Claims, 6 Drawing Sheets

(56) References Cited

U.S. PATENT DOCUMENTS

| | | | |
|---|---|---|---|
| 2006/0023976 A1* | 2/2006 | Alvater | B65D 81/3266 383/210 |
| 2008/0223939 A1* | 9/2008 | Halbur | G06Q 20/34 235/494 |
| 2017/0233157 A1* | 8/2017 | Thobe | B65B 9/20 53/412 |
| 2018/0354683 A1* | 12/2018 | Bludorn | B42D 15/0053 |

* cited by examiner

Fig. 1

Prior Art

TEAR-AWAY PACKAGE FOR FRAGRANCE IMPREGNATED WAFER

RELATED APPLICATIONS

None.

BACKGROUND OF THE INVENTION

Field of the Invention

The present invention relates to methods of manufacture and apparatus for dispersing fragrance compounds. More specifically, the present invention relates to a fragrance compound impregnated porous carrier enclosed within an envelope where a tear initiating feature of the envelope is aligned with a trimmed portion of the porous carrier, to thereby prevent a tear in the envelope from inducing a tear in the porous carrier.

Description of the Related Art

Fragrance compounds are produced and used to disperse fragrances into the air within an ambient environment, such as the interior of an automobile. The dispersed fragrances serve the purposes of presenting pleasurable aromas, freshening the air, concealing objectionable odors, and providing certain therapeutic benefits. Fragrance compounds are comprised of one or more fragrance components and one or more fragrance carrier solutions. The fragrance components combine to produce the desired aroma, such as lemon, cherry, vanilla, and so forth. Individual fragrances typically include from eight to over thirty fragrance components. These components may include fragrance oils, esters, glycols, alcohols, acetate, and so forth. Manufacturers often keep the specific fragrance formulations secret because of the subjective and artistic nature of fragrance development and formulation. Fragrance carrier solutions are used to aid in the vaporization and dispersion of the fragrance components into the air. Various carrier solutions are known, and may include water, alcohols, ethylene glycol, dipropylene glycol, diethyl phthalate, hexylene glycol, and others. The ratio and mixtures of fragrance components and fragrance carriers are also quite specific, depending on the desired intensity of the fragrance, the duration of the dispersion period, and other application factors. Fragrance compound formulations are also commonly held in confidence by fragrance producers.

Once a fragrance compound has been designed and produced, it then must be packaged, delivered, stored and ultimately be dispersed into an ambient environment. One type of packaging is a sealed bottle of a liquid fragrance compound. However, this type of product delivery does not lend itself well to consumer level consumption. The problem is that a bottle of liquid does not include any convenient means for later dispersion of the fragrance at the end user level. A more user friendly approach is to permeate the fragrance compound into physical structure that enables the vaporization and dispersion of the fragrance compound into the air. An example of such a system is disclosed in U.S. Reissue Pat. No. Re39,905 to Mobley for AIR FRESHENER CARD, METHOD OF USE AND METHOD OF MANUFACTURE, the contents of which are hereby incorporated by reference. Mobley is also the inventor of the presently disclosed invention. The U.S. Pat. No. Re39,905 disclosure employs a paperboard card impregnated with air freshener as the physical carrier of the fragrance compound to aid in dispersion of the fragrance by the end user. The cards are impregnated with fragrance compound and then stored in a hermetically sealed bulk container until they are deployed into service. An improvement to this delivery system is the use of individually wrapped fragrance wafers, which are referred to by a trade name, (Wonder Wafers®), for the cards that have been impregnated with fragrance compounds. The fragrance wafers have a logotype or other information imprinted thereon, and are packaged into a transparent film envelope, and sold individually, or in packages containing a small number of individually wrapped cards. The transparent film envelope provides a hermetically sealed environment that contains the card and fragrance compound until the consumer tears open the envelope to retrieve the card and places it into service.

Figure 1:
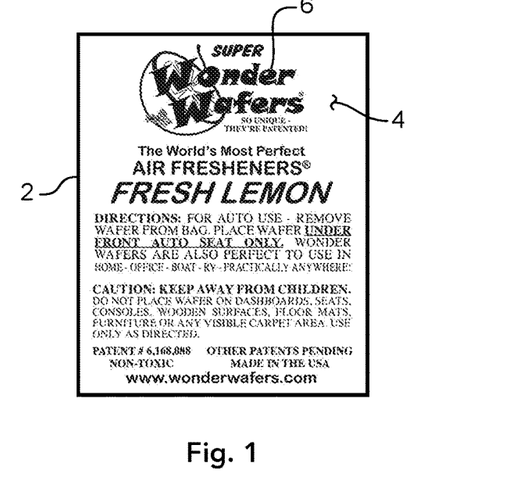
FIG. 1 is a front view drawing of a fragrance wafer according to the prior art.
Figure 2:
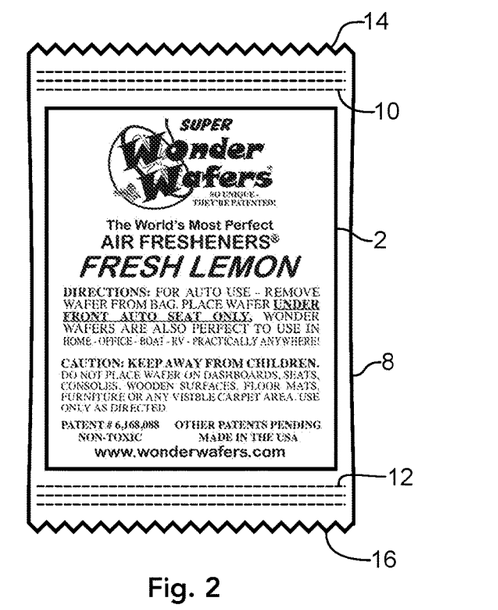
FIG. 2 is a front view drawing of a fragrance wafer within a transparent envelope according to the prior art.
Figure 3:
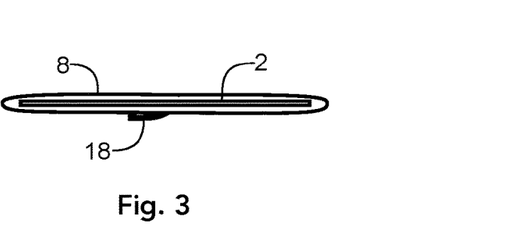
FIG. 3 is a section view drawing of a fragrance wafer within a transparent envelope according to the prior art.

Reference is directed to FIGS. 1 through 4, which are a front view drawing of a fragrance wafer, a front view drawing of a fragrance wafer within a transparent envelope, a section view drawing of a fragrance wafer within a transparent envelope, and a front view drawing of a fragrance wafer within a transparent envelope as it is torn open, respectively, according to the prior art. FIG. 1 illustrates a porous carrier 2, which may be paperboard, blotter paper, or other suitable porous carrier material that is impregnated with a fragrance compound 4, and also has graphic material 6 imprinted thereon. The graphic material 6 may include branding, product description, usage instructions and safety warnings, for example. In FIG. 2 and FIG. 3, the porous carrier 2 (also referred to herein as a "fragrance wafer" or "wafer") is inserted into a transparent envelope 8 that is wrapped about the fragrance wafer 2 and joined together with itself along a spine seam 18 that is thermally fused to form an airtight seal. A first end 14 of the envelope 8 has a serrated cut, which is also referred to as a tear initiating feature. A thermal fusion seal 10 is formed adjacent the first end 14 to hermetically seal that end 14 opening. In the same fashion, second end 16 of the envelope 8 has a serrated cut. A thermal fusion seal 12 is formed adjacent the second end 16 to thereby complete the hermetic sealing of the entire envelope 8. The airtight hermetic seal is important because it contains and preserves the fragrance compounds until the envelope is torn open by and end user.

Figure 4:
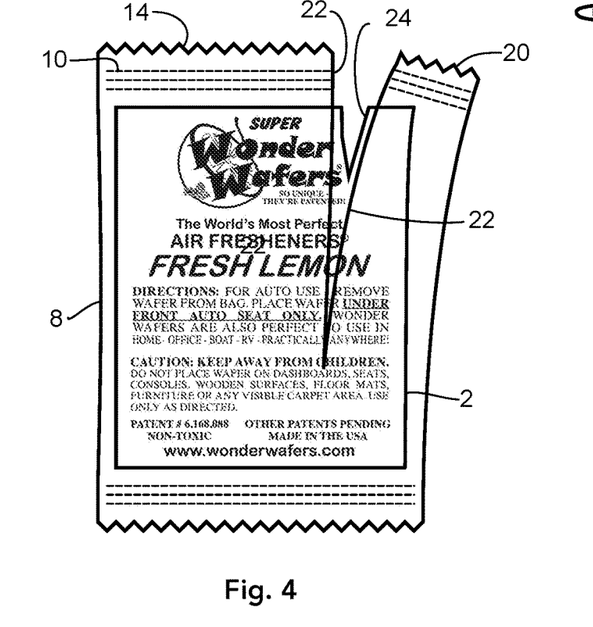
FIG. 4 is a front view drawing of a fragrance wafer within a transparent envelope as it is torn open according to the prior art.

FIG. 4 corresponds with FIG. 1 through 3, but in FIG. 4, the end user has initiated a tear 22 to open the envelope 8 and remove the fragrance wafer 2 therefrom. Note that the serrated ends 14, 16 provide sharp corners in the end cuts 14, 16 that are known to provided plural sharp valley angles in the envelope film, where a tear 22 of the envelope 8 may be most easily initiated. To complete the removal process, the end users grasps either side of a selected tear-open position and tears 22 down the length of the envelope 8 to yield a large enough opening for the fragrance wafer 2 to be removed from the envelope 8. And, herein lies the problem in the prior art. Since the fragrance wafer 2 is a thin piece of paperboard, it also is easily torn, perhaps even more easily that the envelope 8. Too often, this results in a fragrance wafer 8 that is unintentionally torn 24 as the film envelope 8 is torn 22. This results in a degradation of the end product, and results in a less-than-ideal product experience for the end user. Thus, it can be appreciated that there is a need in the art for an improved product that overcomes the problem in the prior art.

SUMMARY OF THE INVENTION

The need in the art is addressed by the apparatuses of the present invention. The present disclosure teaches an apparatus for distributing and dispensing a fragrance compound, which includes a porous carrier that is impregnated with a fragrance compound. The porous carrier is formed as a rectangle of substantially planar and rigid material, but, with a first corner thereof trimmed back from a right angle corner of the rectangle. A film is wrapped about the porous carrier and sealed along a spine seam, and the film is cut at a first end and sealed adjacent thereto, and cut at a second end and sealed adjacent thereto, to thereby form an envelope that is hermetically sealed and impermeable to the fragrance compound. The first end cut includes a first tear initiating feature that establishes a location from which the envelop tears when shear forces are applied adjacent thereto. The porous carrier is positioned within the envelope to align the first corner with the first tear initiating feature such that a tear initiated in the envelope crosses the trimmed back portion of the first corner to thereby prevent the film from initiating a tear in the porous carrier itself.

In a specific embodiment of the foregoing apparatus, the first tear initiating feature is a zigzag cut disposed along a portion of the first end. In another specific embodiment, the first tear initiating feature is a notch cut disposed along a portion of the first end. In yet another specific embodiment, the first tear initiating feature is a slit cut into the first end.

In a specific embodiment of the foregoing apparatus, the trimmed back portion reveals a chamfered edge in place of the first right angled corner. In a refinement to this embodiment, the chamfered edge is aligned at approximately forty-five degrees with respect to two adjacent sides of the porous carrier.

In a specific embodiment of the foregoing apparatus, the trimmed back portion reveals an arcuate edge in place of the first right angled corner. In a refinement to this embodiment, the arcuate edge is convex edge. In another refinement, the arcuate edge is a concave edge.

In a specific embodiment of the foregoing apparatus, the porous carrier is a die cut paperboard card. In another specific embodiment, the film is transparent. In a refinement to this embodiment, the transparent film is polyethylene terephthalate polyester film. In yet another refinement to this embodiment, the transparent film is tear oriented to tear in a direction generally parallel with the spine seam.

In a specific embodiment of the foregoing apparatus, the a porous carrier further includes a second corner having a portion thereof trimmed back from a second right angle corner of the rectangle, and the first end cut further includes a second tear initiating feature, and the porous carrier is positioned within the envelope to align the first corner and the second corner with the first and second tear initiating features.

In a specific embodiment of the foregoing apparatus, the a porous carrier further includes plural corners with portions of each trimmed back from right angled corners of the rectangle, and the first and second end cut further include plural tear initiating features, and the porous carrier is positioned within the envelope to align the plural corners with the plural tear initiating features.

In a specific embodiment of the foregoing apparatus, the trimmed back portion has a width along an edge of the porous carrier, which is parallel to the first end cut, that is in the range of twenty-five to fifty percent of a width of the edge. In a refinement to this embodiment, the tear initiating feature is aligned along the width of the trimmed back portion along the edge of the porous carrier.

The present disclosure teaches a method of distributing and dispensing a fragrance compounds, using a porous carrier impregnated with a fragrance compound where the porous carrier is formed as a rectangle of substantially planar and rigid material. The method includes the steps of trimming back a first corner portion of the porous carrier from a right angle corner of the rectangle, and wrapping a film about the porous carrier and sealing along a spine seam. Then, cutting a first end and second end of the film, and sealing the film adjacent to the first and and the second end cuts, thereby forming an envelope that is hermetically sealed and impermeable to the fragrance compound. The first end cut includes a first tear initiating feature, establishing a location for tearing to begin when shear forces are applied adjacent to the feature. And also, positioning the porous carrier within the envelope and aligning the first corner with the first tear initiating feature, which causes any tear initiated in the envelope to cross the trimmed back portion of the first corner, thereby preventing the film from tearing the porous carrier.

In a specific embodiment of the foregoing method, the trimmed back portion reveals a chamfered edge in place of the first right angled corner. In another specific embodiment, the trimmed back portion reveals an arcuate edge in place of the first right angled corner. In yet another refinement to this embodiment, the method further includes die cutting the porous carrier from paperboard card stock.

DESCRIPTION OF THE INVENTION

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope hereof and additional fields in which the present invention would be of significant utility.

In considering the detailed embodiments of the present invention, it will be observed that the present invention resides primarily in combinations of steps to accomplish various methods or components to form various apparatus and systems. Accordingly, the apparatus and system components, and method steps, have been represented where appropriate by conventional symbols in the drawings, showing only those specific details that are pertinent to understanding the present invention so as not to obscure the disclosure with details that will be readily apparent to those of ordinary skill in the art having the benefit of the disclosures contained herein.

In this disclosure, relational terms such as first and second, top and bottom, upper and lower, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises a" does not, without more constraints, preclude the existence of additional identical elements in the process, method, article, or apparatus that comprises the element.

Figure 5:
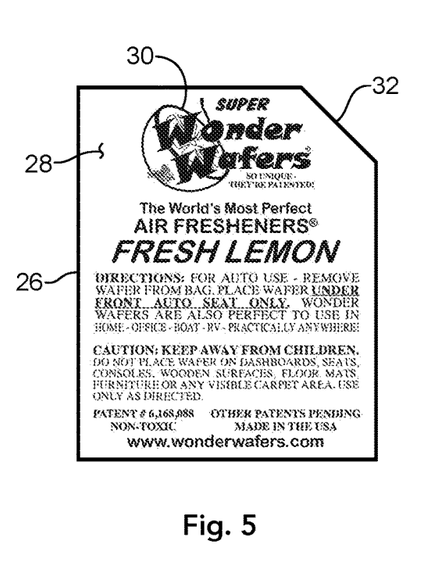
FIG. 5 is a front view drawing of a fragrance wafer according to an illustrative embodiment of the present invention.

Reference is directed to FIG. 5, which is a front view drawing of a fragrance wafer 26, (also referred to generically as a "card"), according to an illustrative embodiment of the present invention. In the illustrative embodiment, the card 26 is a paperboard card, similar to what is known as blotter paper to those skilled in the art, which is semi-rigid and substantially planar and based on a rectangular or square shape with four ninety-degree corners. One of the corners has a portion trimmed back 32 such that a chamfered, or beveled, edge is revealed, which is at an obtuse angle with respect to both of its adjacent sides of the card 26. This angled surface 32, which is a forty-five degree angle in this embodiment, serves a useful function in regards to the improvements in the art taught herein. The card 26 is approximately fifty millimeters by seventy-five millimeters, and approximately one-half millimeter thick in the illustrative embodiment. Other embodiments employ cards that are approximately fifty millimeters square, and fifty millimeters by sixty-seven millimeters. The thickness of the card 26 may range of to three millimeters in thickness. Those skilled in the art will appreciate that the exact size of the card is primarily a design choice. In the exemplary illustrative embodiment, the fifty by seventy-five millimeter card will be discussed. On a first of the card's broad planar surfaces, there is printed a logotype, brand name, manufacturer identity and address, usage instructions and a usage warning, collectively 30. On the second broad planar surface, there may be printed a UPC barcode (not shown). The paperboard material is fibrous and porous, and therefore provides a particularly suitable physical carrier structure for a fragrance compound solution 28, consisting of fragrance components and a fragrance carrier solution. The fragrance wafer 26 is impregnated with the fragrance compounds 28 either prior to packaging, or during the packaging process. In certain illustrative embodiments, the fragrance wafer 26 is fully saturated, and in other embodiments, the fragrance wafer is impregnated with a lesser quantity of fragrance compound solution. The amount of solution utilized is a design choice based on the intended functional parameters of the product, such as the desired intensity of the fragrance release and the duration of its useful effectiveness.

Figure 6:
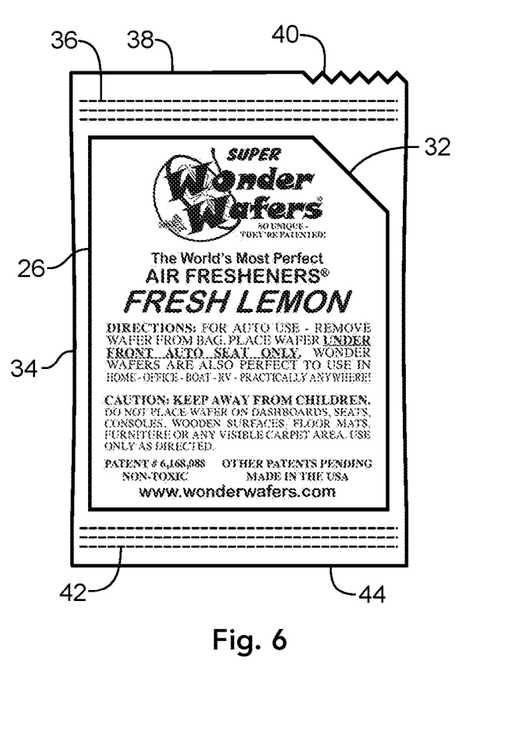
FIG. 6 is a front view drawing of a fragrance wafer within a transparent envelope according to an illustrative embodiment of the present invention.

Reference is directed to FIG. 6, which is a front view drawing of a fragrance wafer 26 within a transparent envelope 34 according to an illustrative embodiment of the present invention. FIG. 6 places the fragrance impregnated wafer 26 discussed with respect to FIG. 5 into a transparent film envelope 34. The transparent film envelope 34 is formed by wrapping a suitable film about the fragrance wafer 26, forming a spine seam and heat sealing it closed (not shown), and then cutting the film to form a first end 38 and a second end 44. In addition, a heat seal closure 36 if formed adjacent the first end 38, and likewise a heat seal closure 42 is formed adjacent the second end 44, thereby completing a hermetically sealed envelope 34.

In FIG. 6, since the fragrance wafer 26 is imprinted with useful information (item 30, FIG. 5), is it beneficial for the envelope 34 to be fabricated from a transparent polymeric film material. This arrangement results in both the utilitarian advantage as well as a beneficial cost controlling measure. The same printed card stock that is used for bulk product sales can also be used for individually packaged product sales. And, the envelope 34 does not have to include or repeat the information imprinted on the card 26. Several suitable transparent film materials are available. Among these are polyethylene terephthalate polyester (commonly referred to as Mylar®), polypropylene film, and cellophane. Note in FIG. 6 that the first end cut 38 comprises a portion thereof with a tear initiating feature 40 along a portion of its width. In this embodiment, the tear initiating feature is a serrated, or zigzag, cut that extends for approximately one-third the width of the first end cut 38. This substantially corresponds with the width of the trimmed back corner portion 32 on the card 26, which presents a chamfered, or beveled, edge as illustrated. This is also approximately one-third the width of the card 26. Note that the trimmed edge 32 and the tear initiating feature 40 are aligned with one another when the card 26 and envelope 34 are assembled together.

Figure 7:
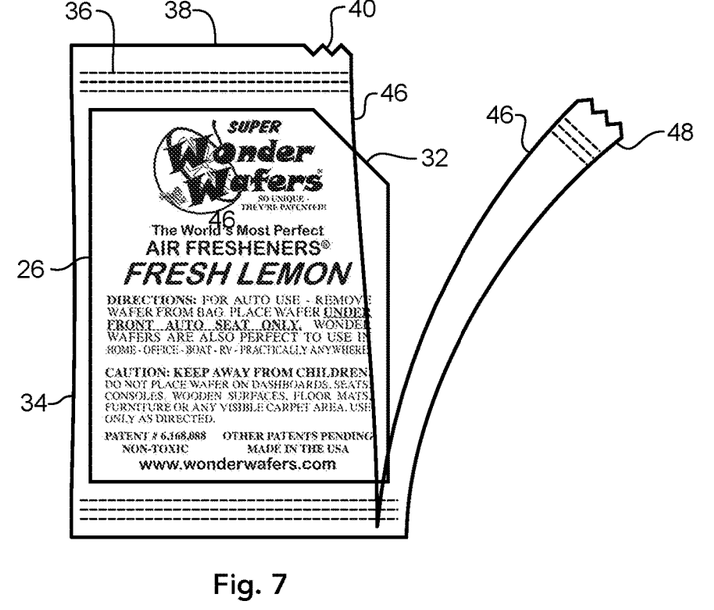
FIG. 7 is a front view drawing of a fragrance wafer within a transparent envelope as it is torn open according to an illustrative embodiment of the present invention.

Reference is directed to FIG. 7, which is a front view drawing of a fragrance wafer 26 within a transparent envelope 34 as it is torn open 46 according to an illustrative embodiment of the present invention. FIG. 7 corresponds with FIG. 6. In FIG. 7, an end user has grasped the envelope 34 about the tear initiating feature 40 and applied a shearing force. The serrated cut 40 portion of the first edge 38 enables a tear 46 to be initiated at one of its sharp valley angles. In the illustrative embodiment, polyethylene terephthalate polyester film that has a directional shear characteristic is employed. That direction is oriented from end 38 to end 44 of the envelope 34, and as such, the tear 46 initiated by the end user proceeds downward (as illustrated) through the envelope 34. As the tear crosses over the top of the card 26, it engages the chamfered edge 32 of the card 26. The chamfered edge 32 directs the film off the side of the card 26, instead of inducing a tear in the card as occurred in prior art embodiment where the top edge of the card was generally orthogonal to the direction of the tear (see FIG. 4). Thusly, the chamfered edge 32 acts an an inclined plane that the film tear edge 46 can graze off of, reducing any tearing forces that might otherwise be induced in the card 26. Once the user tear is complete, the fragrance wafer 26 can be removed from the envelope 34 and placed into service. The use of a serrated, or zigzag, edge is beneficial in this embodiment since it provides a visual cue to the end user as to where to initiate a tear, and of course, that is in the corner of the envelope 34 where the chamfered edge 32 of the fragrance wafer 26 is located.

Figure 8:
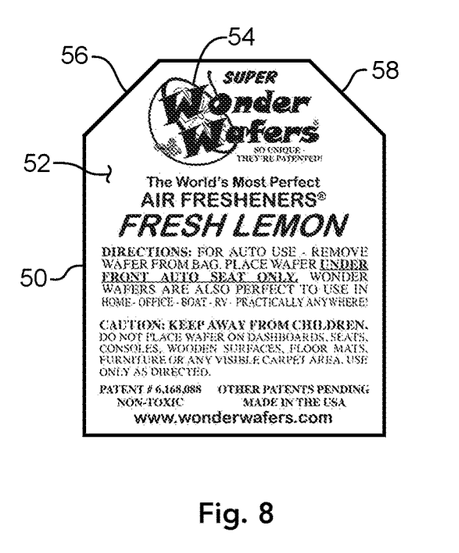
FIG. 8 is a front view drawing of a fragrance wafer according to an illustrative embodiment of the present invention.
Figure 9:
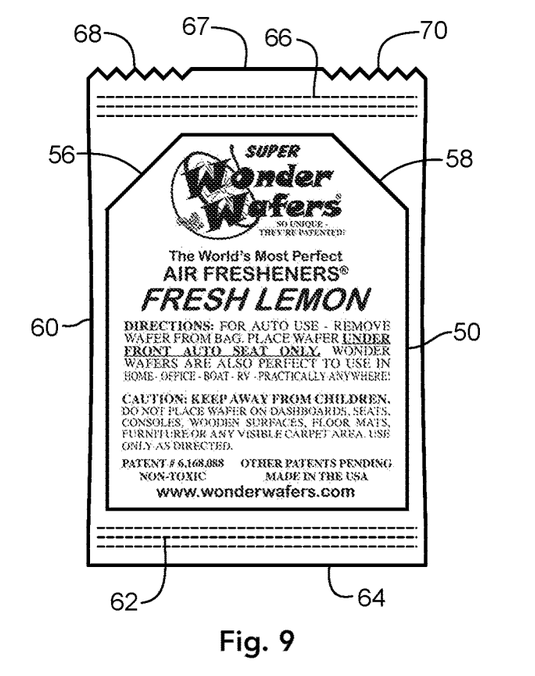
FIG. 9 is a front view drawing of a fragrance wafer within a transparent envelope according to an illustrative embodiment of the present invention.

Reference is directed to FIG. 8 and FIG. 9, which are a front view drawing of a fragrance wafer 50 and a front view drawing of a fragrance wafer 50 within a transparent envelope 60, respectively, according to an illustrative embodiment of the present invention. In FIG. 8, the card 50 is impregnated with fragrance compound 52 and has graphic material 54 imprinted thereon. In this embodiment, two of the corners 56, 58 has been trimmed to reveal two beveled, or chamfered, edges, each at approximately forty-five degree angles, as illustrated. Also, each of the chamfered edges account for approximately twenty-five percent of the width of the top (as illustrated) of the card 50. In FIG. 9, the card 50 has been wrapped with a hermetically sealed envelope 60 that has a first end 67 and a second end 64. A heat seal closure 66 is formed adjacent the first end 67, and likewise, a heat seal closure 62 is formed adjacent the second end 64, thereby completing a hermetically sealed envelope 60. The first end 67 comprises a first tear initiating feature 68 and a second tear initiated feature 70, both of which present a serrated, or zigzag, edge portion that each extend for approximately twenty-five percent of the width of the first edge 67. The tear initiating features 68, 70 align with the trimmed corner portions 56, 58 of the fragrance wafer 50. In this manner, the end user can grasp either of the two serrated portions 68, 70 and apply shear forces thereto to initiate a tear (not shown) and removed the card 50 from the envelope 60. This arrangement is somewhat more versatile than the embodiment on FIG. 7, because it accommodates both right and left handed users in a more comfortable manner.

Figure 10:
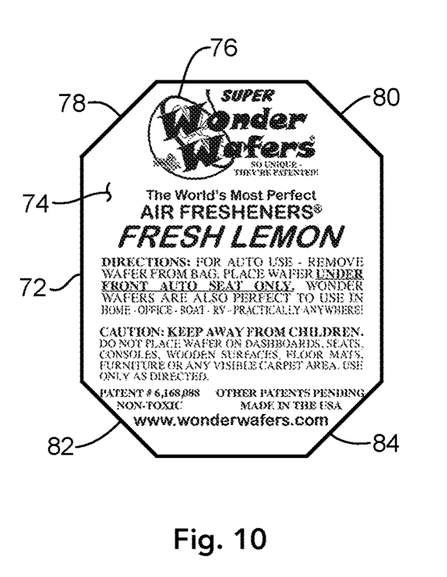
FIG. 10 is a front view drawing of a fragrance wafer according to an illustrative embodiment of the present invention.
Figure 11:
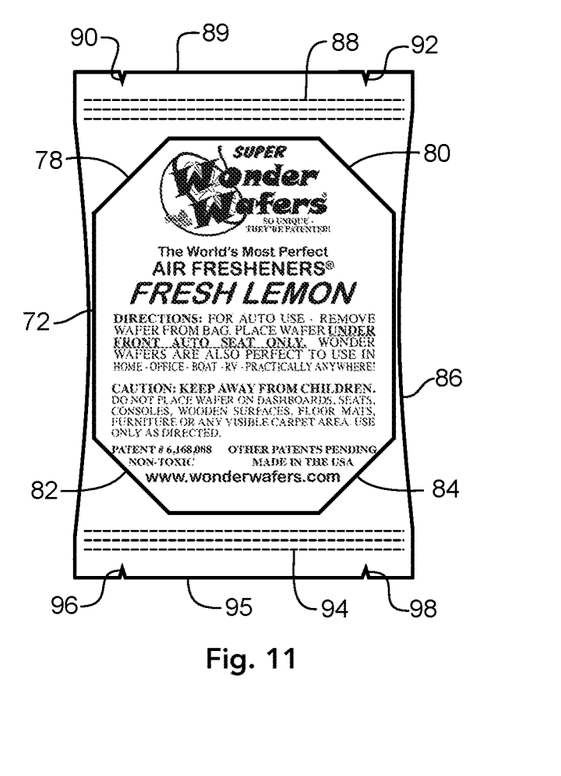
FIG. 11 is a front view drawing of a fragrance wafer within a transparent envelope according to an illustrative embodiment of the present invention.

Reference is directed to FIG. 10 and FIG. 11, which are a front view drawing of a fragrance wafer 72 and a front view drawing of a fragrance wafer 72 within a transparent envelope 86, respectively, according to an illustrative embodiment of the present invention. In FIG. 10, the card 72 is impregnated with fragrance compound 74 and has graphic material 76 imprinted thereon. In this embodiment, four of the corners 78, 80, 82, 84 have been trimmed to reveal four chamfered edges, each at approximately forty-five degree angles, as illustrated. Also, each of the chamfered edges account for approximately twenty-five percent of the width of the top and bottom (as illustrated) of the card 72. In FIG. 11, the card 72 has been wrapped with a hermetically sealed envelope 86 that has a first end 89 and a second end 95. A heat seal closure 88 if formed adjacent the first end 89, and likewise a heat seal closure 94 is formed adjacent the second end 95, thereby completing a hermetically sealed envelope 86. The first end 89 comprises a first tear initiating feature 90 and a second tear initiated feature 92, both of which present a notch or slit in the first edge 89 of the envelope 86. Likewise, the second end 95 comprises a first tear initiating feature 96 and a second tear initiated feature 98, both of which present a notch or slit in the second edge 95 of the envelope 86. The tear initiating features 90, 92, 96, 98 align with the trimmed corner portions 78, 80, 82, 84 of the fragrance wafer 72. In this manner, the end user can grasp the envelope 86 about any of the four notches 90, 92, 96, 98 and apply shear forces thereto to initiate a tear (not shown) and removed the card 72 from the envelope 86. This arrangement is somewhat more versatile than the prior embodiments because it enables the end user to grasp and tear any corner of the envelope 86 to tear it open.

Figure 12:
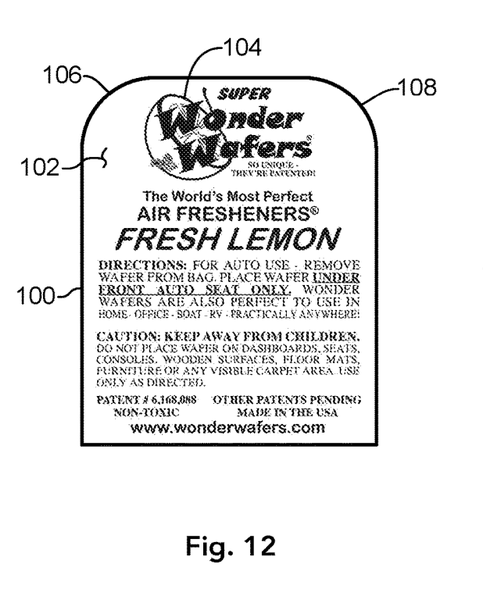
FIG. 12 is a front view drawing of a fragrance wafer according to an illustrative embodiment of the present invention.
Figure 13:
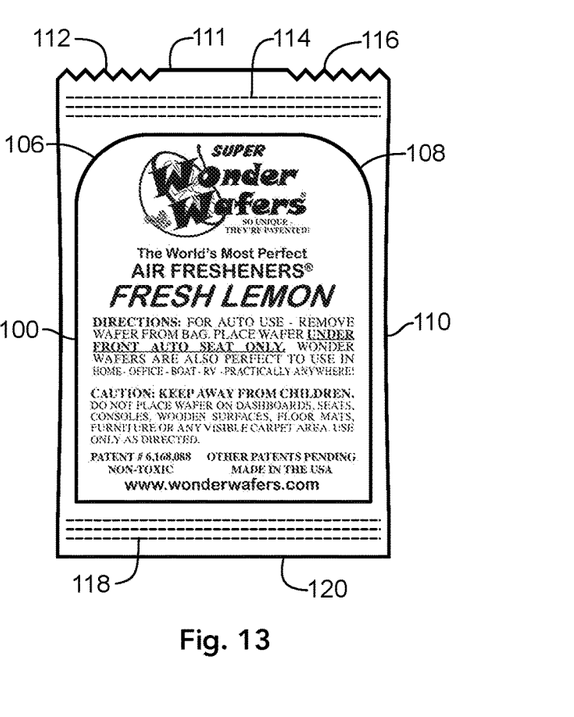
FIG. 13 is a front view drawing of a fragrance wafer within a transparent envelope according to an illustrative embodiment of the present invention.

Reference is directed to FIG. 12 and FIG. 13, which are a front view drawing of a fragrance wafer 100 and a front view drawing of a fragrance wafer 100 within a transparent envelope 110, respectively, according to an illustrative embodiment of the present invention. In FIG. 12, the card 100 is impregnated with fragrance compound 102 and has graphic material 104 imprinted thereon. In this embodiment, two of the corners 106, 108 has been trimmed to reveal two convex arcuate edges, each presenting a rounded edge of approximately ninety degrees, as illustrated. Also, each of the arcuate edges 106, 108 account for approximately twenty-five percent of the width of the top (as illustrated) of the card 100. In FIG. 13, the card 100 has been wrapped with a hermetically sealed envelope 110 that has a first end 111 and a second end 120. A heat seal closure 114 is formed adjacent the first end 111, and likewise, a heat seal closure 118 is formed adjacent the second end 120, thereby completing a hermetically sealed envelope 110. The first end 111 comprises a first tear initiating feature 112 and a second tear initiated feature 116, both of which present a serrated, or zigzag, edge portion that each extend for approximately twenty-five percent of the width of the first edge 111. The tear initiating features 112, 116 align with the trimmed corner portions 106, 108 of the fragrance wafer 100. In this manner, the end user can grasp either of the two serrated portions 112, 116 and apply shear forces thereto to initiate a tear (not shown) and removed the card 100 from the envelope 110. Testing has shown that the arcuate edges 106, 108 are effective at defecting the envelope 110 film over the card 100 without initiating a tear in the card 100. This embodiment has an advantage in that a lesser amount of material is trimmed from the two upper corners 106, 108 of the card 100, leaving more material to absorb fragrance compound 102 and more area on the card 100 surface for the imprinted graphics 104.

Figure 14:
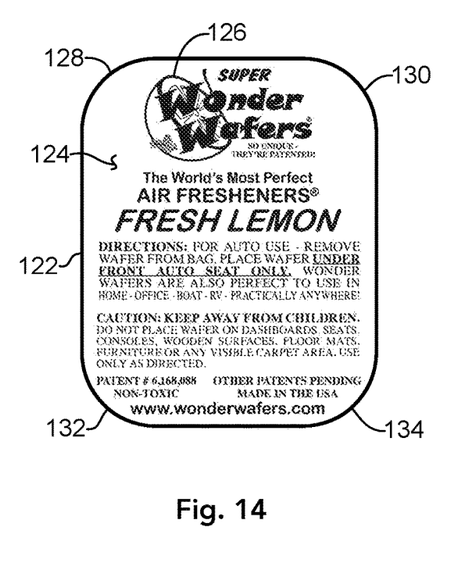
FIG. 14 is a front view drawing of a fragrance wafer according to an illustrative embodiment of the present invention.
Figure 15:
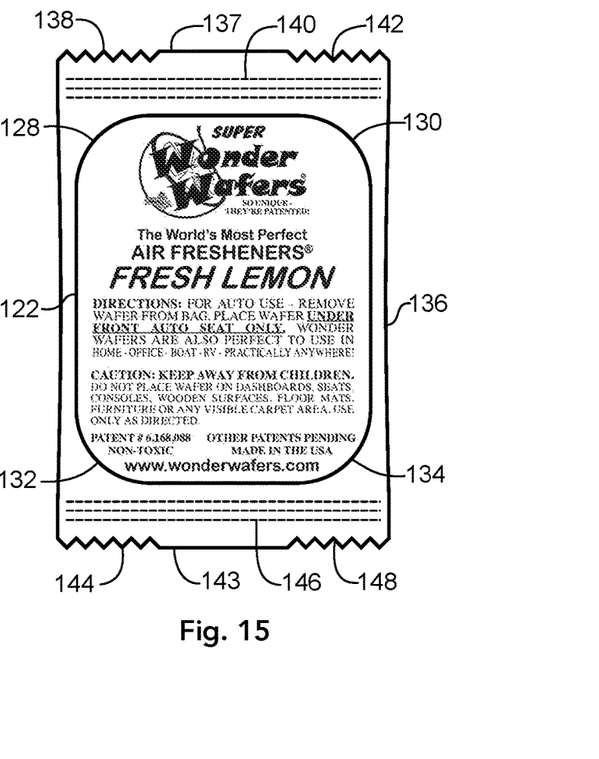
FIG. 15 is a front view drawing of a fragrance wafer within a transparent envelope according to an illustrative embodiment of the present invention.

Reference is directed to FIG. 14 and FIG. 15, which are a front view drawing of a fragrance wafer 122 and a front view drawing of a fragrance wafer 122 within a transparent envelope 136, respectively, according to an illustrative embodiment of the present invention. In FIG. 14, the card 122 is impregnated with fragrance compound 124 and has graphic material 126 imprinted thereon. In this embodiment, four of the corners 128, 130, 132, 134 have been trimmed to reveal four convex arcuate edges, each presenting a rounded edge of approximately ninety degrees, as illustrated. Also, each of the arcuate edges 128, 130, 132, 134 account for approximately twenty-five percent of the width of the top and bottom (as illustrated) of the card 122. In FIG. 15, the card 122 has been wrapped with a hermetically sealed envelope 136 that has a first end 137 and a second end 143. A heat seal closure 140 is formed adjacent the first end 137, and likewise, a heat seal closure 146 is formed adjacent the second end 143, thereby completing a hermetically sealed envelope 136. The first end 137 comprises a first tear initiating feature 138 and a second tear initiated feature 142, both of which present a serrated, or zigzag, edge portion that each extend for approximately twenty-five percent of the width of the first edge 111. Likewise, the second end 143 comprises a third tear initiating feature 144 and a fourth tear initiated feature 148, both of which present a serrated, or zigzag, edge portion that each extend for approximately twenty-five percent of the width of the second edge 143. The tear initiating features 138, 142, 144, 148 align with the trimmed corner portions 128, 130, 132, 134 of the fragrance wafer 122. In this manner, the end user can grasp any of the four serrated portions 138, 142, 144, 148 and apply shear forces thereto to initiate a tear (not shown) and removed the card 122 from the envelope 122.

Figure 16:
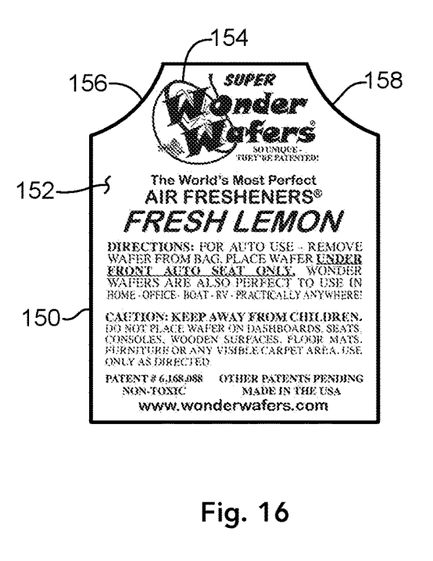
FIG. 16 is a front view drawing of a fragrance wafer according to an illustrative embodiment of the present invention.
Figure 17:
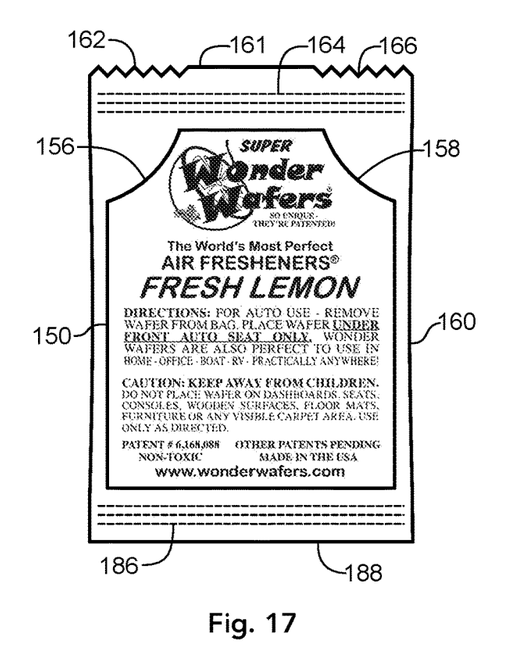
FIG. 17 is a front view drawing of a fragrance wafer within a transparent envelope according to an illustrative embodiment of the present invention.

Reference is directed to FIG. 16 and FIG. 17, which are a front view drawing of a fragrance wafer 150 and a front view drawing of a fragrance wafer 150 within a transparent envelope 160, respectively, according to an illustrative embodiment of the present invention. In FIG. 16, the card 150 is impregnated with fragrance compound 152 and has graphic material 154 imprinted thereon. In this embodiment, two of the corners 156, 158 have been trimmed to reveal two concave arcuate edges, each presenting a scalloped edge, as illustrated. Also, each of the arcuate edges 156, 158 account for approximately twenty-five percent of the width of the top (as illustrated) of the card 150. In FIG. 17, the card 150 has been wrapped with a hermetically sealed envelope 160 that has a first end 161 and a second end 188. A heat seal closure 164 is formed adjacent the first end 161, and likewise, a heat seal closure 186 is formed adjacent the second end 188, thereby completing a hermetically sealed envelope 160. The first end 161 comprises a first tear initiating feature 162 and a second tear initiated feature 166, both of which present a serrated, or zigzag, edge portion that each extend for approximately twenty-five percent of the width of the first edge 161. The tear initiating features 162, 166 align with the trimmed corner portions 156, 158 of the fragrance wafer 150. In this manner, the end user can grasp either of the two serrated portions 162, 166 and apply shear forces thereto to initiate a tear (not shown) and removed the card 150 from the envelope 160. Testing has shown that the concave arcuate edges 156, 158 are effective at defecting the envelope 160 film over the card 150 without initiating a tear in the card 150.

Figure 18:
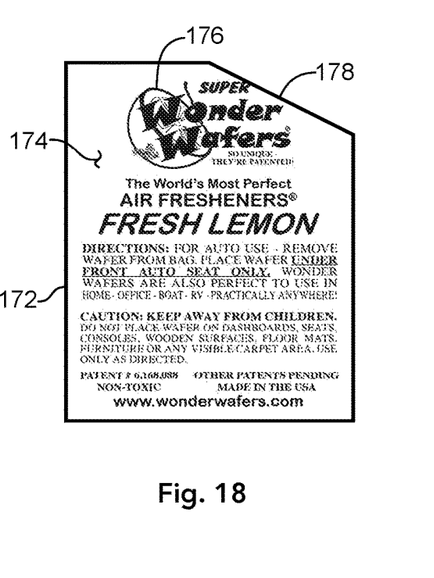
FIG. 18 is a front view drawing of a fragrance wafer according to an illustrative embodiment of the present invention.
Figure 19:
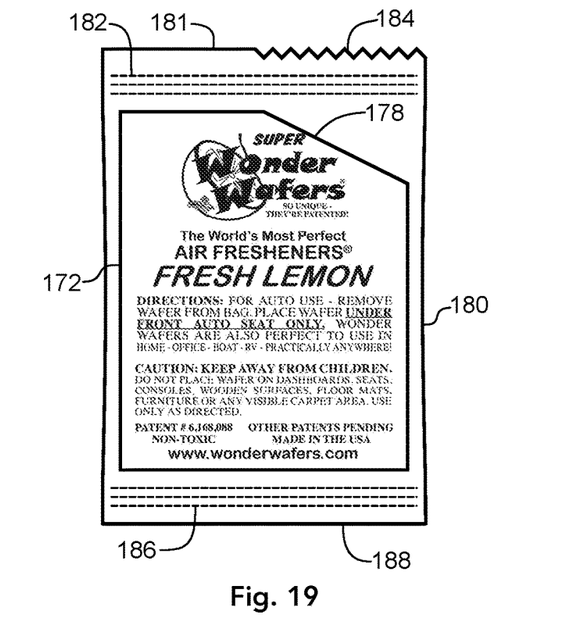
FIG. 19 is a front view drawing of a fragrance wafer within a transparent envelope according to an illustrative embodiment of the present invention.

Reference is directed to FIG. 18 and FIG. 19, which are a front view drawing of a fragrance wafer 172 and a front view drawing of a fragrance wafer 172 within a transparent envelope 180, respectively, according to an illustrative embodiment of the present invention. In FIG. 18, the card 172 is impregnated with fragrance compound 174 and has graphic material 176 imprinted thereon. In this embodiment, one of the corners 178 has been trimmed to reveal a chamfered edge that forms an acute angle with the top of the card 172 (as illustrated) and an obtuse angle with respect to the side of the card 712 (as illustrated). The chamfered edges accounts for approximately fifty percent of the width of the top (as illustrated) of the card 172. In FIG. 19, the card 172 has been wrapped with a hermetically sealed envelope 180 that has a first end 181 and a second end 188. A heat seal closure 182 is formed adjacent the first end 181, and likewise, a heat seal closure 186 is formed adjacent the second end 188, thereby completing a hermetically sealed envelope 180. The first end 181 comprises a first tear initiating feature 184, which present a serrated, or zigzag, edge portion that each extends for approximately fifty percent of the width of the first edge 181. The tear initiating feature 184 aligns with the trimmed corner portion 178 of the fragrance wafer 172. In this manner, the end user can grasp the serrated portion 184 and apply shear forces thereto to initiate a tear (not shown) and removed the card 172 from the envelope 180.

Figure 20:
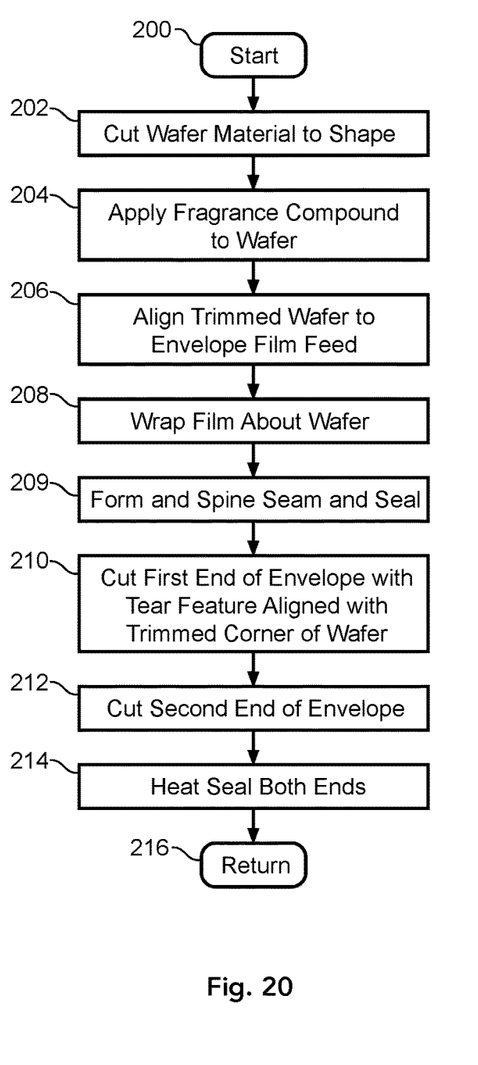
FIG. 20 is a process flow diagram for placing an envelope about a fragrance wafer according to an illustrative embodiment of the present invention.

Reference is directed to FIG. 20, which is a process flow diagram for placing an envelope about a fragrance wafer according to an illustrative embodiment of the present invention. The process starts at step 200 and proceeds to step 202 where a wafer is cut from a sheet of suitable paperboard, including a trimmed corner of the wafer. At step 204, the fragrance compound is applied to the wafer and immediately begins to be absorbed into the wafer. At step 206, the wafer with trimmed corner is aligned with the transparent film feed to begin the process of forming the hermetically sealed envelope. At step 208, the film is wrapped about the wafer using an envelope wrapping machine. At step 209, the rear spine is formed and a heat seal process seals the rear spine. At step 210, the first end in the film is cut with the tear initiating feature aligned with the trimmed corner of the wafer. At step 212, the second end of the wafer is cut. At step 214, both ends of the envelop are heat sealed to perfect the hermetically sealed envelope. The process returns at step 216.

Figure 21:
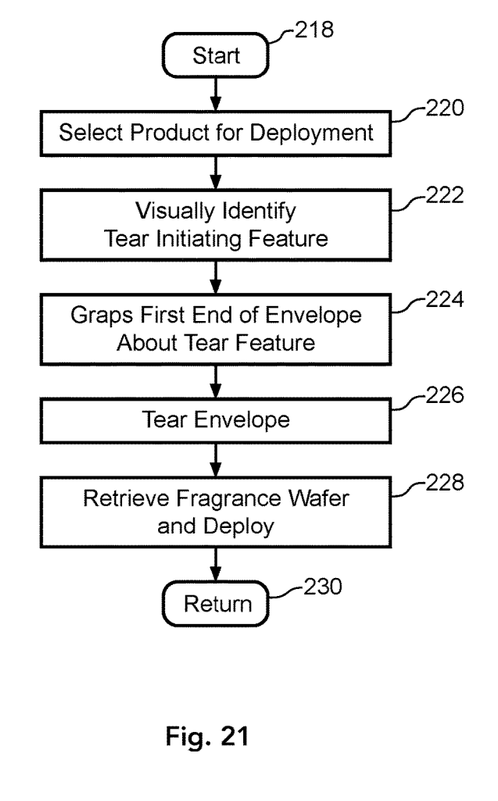
FIG. 21 is a process flow diagram for removing a fragrance wafer from an envelope according to an illustrative embodiment of the present invention.

Reference is directed to FIG. 21, which is a process flow diagram for removing a fragrance wafer from an envelope according to an illustrative embodiment of the present invention. The process starts at step 218 and proceeds to step 220 where an enveloped fragrance wafer is selected for deployment by an end user. At step 222, the user visually identifies the tear initiating feature, and at step 224, the end user grasps the envelope about the tear initiating feature and applies shear forces. At step 226, the envelope is torn over the trimmed corner of the fragrance wafer. At step 228 the wafer is retrieved from the envelope and deployed. The process returns at step 230.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. An apparatus for distributing and dispensing a fragrance compound, comprising:
    a porous carrier impregnated with a fragrance compound, wherein said porous carrier is formed as a rectangle of substantially planar and rigid material, having at least a first right angle corner trimmed back to reveal a chamfered edge, which lies at an obtuse angle with respect to two adjacent sides of said rectangle, and wherein the width of said chamfered edge along one of said two adjacent sides is in the range of 25% to 50% of said one adjacent side length prior to being trimmed;

a film wrapped about said porous carrier and sealed along a spine seam, and cut at a first end and sealed adjacent thereto, and cut at a second end and sealed adjacent thereto, to thereby form an envelope that is hermetically sealed and impermeable to said fragrance compound, and wherein said film possesses a directional shear characteristic that is oriented to tear in parallel with said spine seam, and wherein said first end cut comprises a first serrated edge portion that defines plural serration valley angles and that has a width in the range of 25% to 50% of said first end cut length, and which provides a visual cue as to where to initiate a tear in said envelope when shear forces are applied adjacent thereto, and wherein said first end cut further comprises a first non-serrated edge portion having a width in the range of 75% to 50% of said first end cut, correspondingly, and wherein said porous carrier is positioned within said envelope to align said chamfered edge with said first serrated edge portion such that a tear initiated in said envelope crosses said chamfered edge to thereby prevent said film from initiating a tear in said porous carrier.

2. The apparatus of claim 1, and wherein:
said chamfered edge is aligned at approximately one hundred and thirty-five degrees with respect to said two adjacent sides of said porous carrier.

3. The apparatus of claim 1, and wherein:
said porous carrier is a die cut paperboard card.

4. The apparatus of claim 1, and wherein:
said porous carrier further includes a second right angle corner trimmed back to reveal a second chamfered edge of said rectangle, and wherein
said first end cut further comprises a second serrated edge portion along said first end cut length, and having said first non-serrated edge portion disposed between said first and second serrated edge portions, and wherein
said porous carrier is positioned within said envelope to align said second chamfered edge with said second serrated edge portion.

5. The apparatus of claim 1, and wherein:
said porous carrier further includes plural right angle corners trimmed back to reveal corresponding chamfered edges of said rectangle, and wherein
said first end cut further comprises a second serrated edge portion along said first end cut length, and having said first non-serrated edge portion disposed between said first and second serrated edge portions, and wherein said second end cut further comprises third and fourth serrated edge portions along said second end cut length, and having a second non-serrated edge portion disposed between said third and fourth serrated edge portions, and wherein said porous carrier is positioned within said envelope to align said plural corners with said second, third, and fourth serrated edge portions.

6. The apparatus of claim 1, and wherein:
said porous carrier has a graphic imprinted thereon and said film is transparent.

7. The apparatus of claim 1, and wherein:
said transparent film is polyethylene terephthalate polyester film.

8. A method of distributing and dispensing a fragrance compound, using a porous carrier impregnated with a fragrance compound, wherein the porous carrier is formed as a rectangle of substantially planar and rigid material, the method comprising the steps of:

trimming back at least a first corner portion of the porous carrier, thereby revealing a chamfered edge that lies at an obtuse angle with respect to two adjacent sides of the rectangle, wherein the width of the chamfered edge along one of said two adjacent sides is in the range of 25% to 50% of the one adjacent side prior to trimming;

wrapping a film about the porous carrier and sealing along a spine seam, wherein the film possesses a directional shear characteristic, and orienting the film to tear in parallel with the spine seam;

cutting a first end and second end of the film, and sealing the film adjacent to the first and the second end cuts, thereby forming an envelope that is hermetically sealed and impermeable to the fragrance compound, and wherein the first end cut includes a serrated portion that defines plural serration valley angles, wherein the serrated portion has a width in the range of 25% to 50% of the first end cut length, thereby providing a visual cue for initiating a tear in the envelope, and wherein the first end cut further includes a non-serrated edge portion having a width in the range of 75% to 50% of the first end cut, correspondingly, and positioning the porous carrier within the envelope and aligning the chamfered edge with the serrated portion, thereby causing a tear initiated in the envelope to cross the chamfered edge of the first corner, thereby preventing the film from tearing the porous carrier.

9. The method of claim 8, further comprising the step of:
die cutting the porous carrier from paperboard card stock.

* * * * *